United States Patent
Pagès et al.

(10) Patent No.: US 9,364,600 B2
(45) Date of Patent: Jun. 14, 2016

(54) SYSTEM AND METHOD FOR OPTIMIZED APHERESIS DRAW AND RETURN

(71) Applicant: Haemonetics Corporation, Braintree, MA (US)

(72) Inventors: Etienne Pagès, Cessy (FR); Michael Ragusa, Hingham, MA (US)

(73) Assignee: Haemonetics Corporation, Braintree, MA (US)

( * ) Notice: Subject to any disclaimer, the term of this patent is extended or adjusted under 35 U.S.C. 154(b) by 110 days.

(21) Appl. No.: 14/167,267

(22) Filed: Jan. 29, 2014

(65) Prior Publication Data

US 2014/0148750 A1 May 29, 2014

Related U.S. Application Data

(62) Division of application No. 13/076,882, filed on Mar. 31, 2011, now Pat. No. 8,647,289, which is a division of application No. 12/102,427, filed on Apr. 14, 2008, now Pat. No. 8,702,637.

(51) Int. Cl.
*A61M 1/14* (2006.01)
*A61M 1/30* (2006.01)
(Continued)

(52) U.S. Cl.
CPC ............... *A61M 1/30* (2013.01); *A61M 1/1601* (2014.02); *A61M 1/1603* (2014.02);
(Continued)

(58) Field of Classification Search
CPC ..... A61M 1/024; A61M 1/0245; A61M 1/14; A61M 1/1601; A61M 1/1603; A61M 1/1613; A61M 1/30; A61M 1/3472; A61M 1/36; A61M 1/3607; A61M 1/3621; A61M 1/3639; A61M 1/3663; A61M 1/3679; A61M 1/382; A61M 2205/3331; A61M 2205/3344; A61M 2205/3351; A61M 2205/3355
See application file for complete search history.

(56) References Cited

U.S. PATENT DOCUMENTS 1,025,059 A 4/1912 Hatton et al.
1,611,725 A 12/1926 Degerth et al.
(Continued)

FOREIGN PATENT DOCUMENTS

CN 2735985 Y 10/2005 ............. A61M 1/38
EP 0 128 683 A2 12/1984 ............. A61M 1/03
(Continued)

OTHER PUBLICATIONS

European Patent Office Alessandro Germano, Authorized officer, International Search Report—Application No. PCT/US2009/040199, dated Sep. 10, 2009 (15 pages), including Written Opinion of the International Searching Authority.
(Continued)

*Primary Examiner* — Adam Marcetich
(74) *Attorney, Agent, or Firm* — Sunstein Kann Murphy & Timbers LLP

(57) ABSTRACT

A blood processing device includes a venous-access device, a blood component separation device, a return line, a draw line, a first pressure sensor, a second pressure sensor, and a first pump. The first pressure sensor is located on the return line between the blood component separation device and the venous-access device, and determines a first pressure. The second pressure sensor is located on the draw line between the blood component separation device and the venous-access device, and determines a second pressure. The first pump is connected to at least one of the return line and the draw line and controls a flow rate within the connected line based on a subject access pressure determined based upon the first and second pressures.

12 Claims, 7 Drawing Sheets

(51) Int. Cl.
*A61M 1/16* (2006.01)
*A61M 1/34* (2006.01)
*A61M 1/36* (2006.01)
*A61M 1/38* (2006.01)
*A61M 1/02* (2006.01)

(52) U.S. Cl.
CPC .......... *A61M 1/1613* (2014.02); *A61M 1/3472* (2013.01); *A61M 1/36* (2013.01); *A61M 1/3621* (2013.01); *A61M 1/3639* (2013.01); *A61M 1/3679* (2013.01); *A61M 1/382* (2013.01); *A61M 1/024* (2013.01); *A61M 1/0245* (2013.01); *A61M 1/14* (2013.01); *A61M 1/3663* (2013.01); *A61M 2205/3331* (2013.01); *A61M 2205/3344* (2013.01); *A61M 2205/3351* (2013.01); *A61M 2205/3355* (2013.01)

(56) References Cited

U.S. PATENT DOCUMENTS

| | | | |
|---|---|---|---|
| 2,087,778 A | 7/1937 | Nelin | 210/64 |
| 2,661,150 A | 12/1953 | Abbott, Jr. | 233/27 |
| 2,750,107 A | 6/1956 | More | 233/2 |
| 2,792,172 A | 5/1957 | Tait | 233/2 |
| 3,096,283 A | 7/1963 | Hein | 233/20 |
| 3,145,713 A | 8/1964 | Latham, Jr. | 128/214 |
| 3,239,136 A | 3/1966 | Hein | 233/20 |
| 3,244,362 A | 4/1966 | Hein | 233/27 |
| 3,244,363 A | 4/1966 | Hein | 233/28 |
| 3,409,213 A | 11/1968 | Latham, Jr. | 233/21 |
| 3,456,875 A | 7/1969 | Hein | 233/24 |
| 3,489,145 A | 1/1970 | Judson et al. | 128/214 |
| 3,565,330 A | 2/1971 | Latham, Jr. | 233/21 |
| 3,655,058 A | 4/1972 | Novak | 210/360 |
| 3,737,096 A | 6/1973 | Jones et al. | 233/19 A |
| 3,774,840 A | 11/1973 | Boatright | 233/14 R |
| 3,987,961 A | 10/1976 | Sinn et al. | 233/27 |
| 4,007,871 A | 2/1977 | Jones et al. | 233/27 |
| 4,010,894 A | 3/1977 | Kellogg et al. | 233/27 |
| 4,014,497 A | 3/1977 | Spiewok et al. | 233/20 R |
| 4,040,965 A | 8/1977 | Kohlheb | 210/297 |
| 4,056,224 A | 11/1977 | Lolachi | 233/14 R |
| 4,082,217 A | 4/1978 | Westberg | 233/25 |
| 4,086,924 A | 5/1978 | Latham, Jr. | 128/214 R |
| 4,140,268 A | 2/1979 | Lacour | 233/1 |
| 4,142,670 A | 3/1979 | Ishimaru et al. | 233/20 R |
| 4,151,844 A | 5/1979 | Cullis et al. | 128/214 R |
| 4,197,847 A | 4/1980 | Djerassi | 128/214 R |
| 4,285,464 A | 8/1981 | Latham, Jr. | 233/26 |
| 4,300,717 A | 11/1981 | Latham, Jr. | 233/1 A |
| 4,303,193 A | 12/1981 | Latham, Jr. | 233/23 A |
| 4,321,921 A | 3/1982 | Laszczower | 128/276 |
| 4,387,848 A | 6/1983 | Kellogg et al. | 494/81 |
| 4,425,114 A | 1/1984 | Schoendorfer et al. | 604/7 |
| 4,430,072 A | 2/1984 | Kellogg et al. | 494/45 |
| 4,447,221 A | 5/1984 | Mulzet | 494/45 |
| 4,457,747 A | 7/1984 | Tu | 604/4 |
| 4,464,167 A | 8/1984 | Schoendorfer et al. | 604/6 |
| 4,466,888 A | 8/1984 | Verkaart | 210/232 |
| 4,482,342 A | 11/1984 | Lueptow et al. | 494/21 |
| 4,490,135 A | 12/1984 | Troutner | 604/5 |
| 4,530,691 A | 7/1985 | Brown | 494/45 |
| 4,534,863 A | 8/1985 | Bacon et al. | 210/232 |
| 4,643,714 A | 2/1987 | Brose | 604/4 |
| 4,647,279 A | 3/1987 | Mulzet et al. | 494/45 |
| 4,655,742 A | 4/1987 | Vantard | 604/6 |
| 4,680,025 A | 7/1987 | Kruger et al. | 604/6 |
| 4,684,361 A | 8/1987 | Feldman et al. | 494/41 |
| 4,687,580 A | 8/1987 | Malbrancq et al. | 210/651 |
| 4,692,136 A | 9/1987 | Feldman et al. | 494/38 |
| 4,708,712 A | 11/1987 | Mulzet | 494/45 |
| 4,713,176 A | 12/1987 | Schoendorfer et al. | 210/645 |
| 4,734,089 A | 3/1988 | Cullis | 494/27 |
| 4,740,202 A | 4/1988 | Stacey et al. | 604/119 |
| 4,740,313 A | 4/1988 | Schoendorfer et al. | 210/651 |
| 4,755,300 A | 7/1988 | Fischel et al. | 210/650 |
| 4,767,396 A | 8/1988 | Powers | 494/60 |
| 4,795,419 A | 1/1989 | Yawn et al. | 494/84 |
| 4,795,448 A | 1/1989 | Stacey et al. | 604/319 |
| 4,806,247 A | 2/1989 | Schoendorfer et al. | 210/321.18 |
| 4,806,252 A | 2/1989 | Brown et al. | 210/744 |
| 4,808,307 A | 2/1989 | Fischel et al. | 210/321.68 |
| 4,850,995 A | 7/1989 | Tie et al. | 604/6 |
| 4,869,812 A | 9/1989 | Schoendorfer et al. | 210/321.63 |
| 4,871,462 A | 10/1989 | Fischel et al. | 210/651 |
| 4,876,013 A | 10/1989 | Shmidt et al. | 210/650 |
| 4,889,524 A | 12/1989 | Fell et al. | 494/12 |
| 4,911,833 A | 3/1990 | Schoendorfer et al. | 210/167 |
| 4,934,995 A | 6/1990 | Cullis | 494/45 |
| 4,940,543 A | 7/1990 | Brown et al. | 210/369 |
| 4,943,273 A | 7/1990 | Pages | 494/41 |
| 4,968,295 A | 11/1990 | Neumann | 604/6 |
| 4,983,156 A | 1/1991 | Knelson | 494/28 |
| 4,983,158 A | 1/1991 | Headley | 494/41 |
| 4,985,153 A | 1/1991 | Kuroda et al. | 210/782 |
| 4,994,188 A | 2/1991 | Prince | 210/636 |
| 5,039,401 A | 8/1991 | Columbus et al. | 210/117 |
| 5,045,048 A | 9/1991 | Kaleskas et al. | 494/41 |
| 5,098,372 A | 3/1992 | Jonsson | 604/5 |
| 5,098,373 A | 3/1992 | Polaschegg | 604/5 |
| 5,100,372 A | 3/1992 | Headley | 494/41 |
| 5,100,564 A | 3/1992 | Pall et al. | 210/782 |
| 5,112,298 A | 5/1992 | Prince et al. | 604/6 |
| 5,114,396 A | 5/1992 | Unger et al. | 494/37 |
| 5,135,667 A | 8/1992 | Schoendorfer | 210/782 |
| 5,141,486 A | 8/1992 | Antwiler | 494/37 |
| 5,147,290 A | 9/1992 | Jonsson | 604/5 |
| 5,154,716 A | 10/1992 | Bauman et al. | 604/410 |
| 5,174,894 A | 12/1992 | Ohsawa et al. | 210/86 |
| 5,194,145 A | 3/1993 | Schoendorfer | 210/90 |
| 5,217,426 A | 6/1993 | Bacehowski et al. | 494/45 |
| 5,217,427 A | 6/1993 | Cullis | 494/45 |
| 5,234,403 A | 8/1993 | Yoda et al. | 604/4 |
| 5,254,248 A | 10/1993 | Nakamura | 210/321.67 |
| 5,273,517 A | 12/1993 | Barone et al. | 494/37 |
| 5,277,701 A | 1/1994 | Christie et al. | 604/4 |
| 5,298,016 A | 3/1994 | Gordon | 604/4 |
| 5,298,171 A | 3/1994 | Biesel | 210/739 |
| 5,300,060 A | 4/1994 | Nelson | 604/410 |
| 5,316,540 A | 5/1994 | McMannis et al. | 494/37 |
| 5,318,511 A | 6/1994 | Riquier et al. | 604/4 |
| 5,318,512 A | 6/1994 | Neumann | 604/6 |
| 5,368,542 A | 11/1994 | McMannis et al. | 494/45 |
| 5,368,555 A | 11/1994 | Sussman et al. | 604/4 |
| 5,386,734 A | 2/1995 | Pusinelli | 73/863.21 |
| 5,387,174 A | 2/1995 | Rochat | 494/10 |
| 5,387,187 A | 2/1995 | Fell et al. | 604/6 |
| 5,403,272 A | 4/1995 | Deniega et al. | 604/4 |
| 5,405,308 A | 4/1995 | Headley et al. | 494/67 |
| 5,417,650 A | 5/1995 | Gordon | 604/4 |
| 5,431,814 A | 7/1995 | Jorgensen | 210/399 |
| 5,437,598 A | 8/1995 | Antwiler | 494/1 |
| 5,437,624 A | 8/1995 | Langley | 604/4 |
| 5,462,667 A | 10/1995 | Wollinsky et al. | 210/645 |
| 5,470,483 A | 11/1995 | Bene et al. | 210/741 |
| 5,484,396 A | 1/1996 | Naficy | 604/4 |
| 5,494,592 A | 2/1996 | Latham, Jr. et al. | 210/805 |
| 5,505,685 A | 4/1996 | Antwiler | 494/37 |
| 5,514,070 A | 5/1996 | Pages | 494/41 |
| 5,543,062 A | 8/1996 | Nishimura | 210/782 |
| 5,551,941 A | 9/1996 | Howell | 494/16 |
| 5,585,007 A | 12/1996 | Antanavich et al. | 210/782 |
| 5,607,579 A | 3/1997 | Latham, Jr. et al. | 210/195.1 |
| 5,643,193 A | 7/1997 | Papillon et al. | 604/6 |
| 5,649,903 A | 7/1997 | Deniega et al. | 604/4 |
| 5,651,766 A | 7/1997 | Kingsley et al. | 604/6 |
| 5,656,163 A | 8/1997 | Brown | 210/360.1 |
| 5,665,061 A | 9/1997 | Antwiler | 604/4 |
| 5,728,060 A | 3/1998 | Kingsley et al. | 604/4 |
| 5,733,253 A | 3/1998 | Headley et al. | 604/4 |
| 5,733,446 A | 3/1998 | Holm | 210/206 |
| 5,733,545 A | 3/1998 | Hood, III | 424/93.72 |
| 5,738,792 A | 4/1998 | Schoendorfer | 210/651 |

(56) References Cited

U.S. PATENT DOCUMENTS

| | | | | |
|---|---|---|---|---|
| 5,762,791 | A | 6/1998 | Deniega et al. | 210/321.67 |
| 5,779,660 | A | 7/1998 | Kingsley et al. | 604/6 |
| 5,783,085 | A | 7/1998 | Fischel | 210/651 |
| 5,792,351 | A | 8/1998 | Wehrle et al. | 210/321.67 |
| 5,882,289 | A | 3/1999 | Sakota et al. | 494/41 |
| 5,906,589 | A | 5/1999 | Gordon et al. | 604/65 |
| 5,919,125 | A | 7/1999 | Berch | 494/67 |
| 5,964,724 | A | 10/1999 | Rivera et al. | 604/4 |
| 5,980,760 | A | 11/1999 | Min et al. | 210/782 |
| 6,007,725 | A | 12/1999 | Brown | 210/739 |
| 6,059,979 | A | 5/2000 | Brown | 210/739 |
| 6,207,063 | B1 | 3/2001 | Brown | 210/739 |
| 6,234,989 | B1 | 5/2001 | Brierton et al. | 604/5.01 |
| 6,251,284 | B1 | 6/2001 | Bischof et al. | 210/739 |
| 6,296,602 | B1 | 10/2001 | Headley | 494/37 |
| 6,464,624 | B2 | 10/2002 | Pages | 494/36 |
| 6,497,676 | B1 | 12/2002 | Childers et al. | 604/29 |
| 6,558,307 | B2 | 5/2003 | Headley | 494/37 |
| 6,623,443 | B1 | 9/2003 | Polaschegg | 604/5.04 |
| 6,743,192 | B1 | 6/2004 | Sakota et al. | 604/6.01 |
| 6,817,984 | B2 | 11/2004 | Robinson et al. | 604/4.01 |
| 7,270,645 | B2 | 9/2007 | Langley et al. | 604/6.01 |
| 7,704,454 | B1 | 4/2010 | Langley et al. | 422/44 |
| 2001/0027156 | A1 | 10/2001 | Egozy et al. | 494/37 |
| 2002/0120227 | A1 | 8/2002 | Childers et al. | 604/29 |
| 2002/0128582 | A1 | 9/2002 | Farrell et al. | 604/6.01 |
| 2002/0156464 | A1 | 10/2002 | Blischak et al. | 604/892.1 |
| 2003/0055375 | A1 | 3/2003 | Holst et al. | 604/67 |
| 2003/0066807 | A1 | 4/2003 | Suzuki | 210/782 |
| 2003/0175150 | A1 | 9/2003 | Grimm | 422/44 |
| 2003/0216683 | A1 | 11/2003 | Shekalim | 604/67 |
| 2003/0229302 | A1 | 12/2003 | Robinson et al. | 604/4.01 |
| 2004/0147865 | A1 | 7/2004 | Cianci et al. | 604/6.01 |
| 2004/0186409 | A1* | 9/2004 | Cavalcanti | A61M 1/3621 604/4.01 |
| 2005/0096578 | A1* | 5/2005 | Kleinekofort | A61M 1/3658 604/4.01 |
| 2005/0235733 | A1 | 10/2005 | Holst et al. | 73/1.16 |
| 2006/0155236 | A1 | 7/2006 | Gara et al. | 604/4.01 |
| 2007/0078370 | A1 | 4/2007 | Shener et al. | 604/8 |
| 2007/0112289 | A1 | 5/2007 | Cavalcanti et al. | 604/4.01 |
| 2008/0146993 | A1 | 6/2008 | Krishna | 604/65 |
| 2008/0275377 | A1* | 11/2008 | Paolini | A61M 1/1086 604/6.11 |
| 2009/0259164 | A1 | 10/2009 | Pages et al. | 604/6.04 |
| 2009/0292236 | A1* | 11/2009 | Kleinekofort | A61M 1/3653 604/6.16 |

FOREIGN PATENT DOCUMENTS

| | | | | |
|---|---|---|---|---|
| EP | 0 171 749 | A1 | 2/1986 | A61M 1/00 |
| EP | 0 208 061 | A1 | 1/1987 | A61M 1/34 |
| EP | 0 257 755 | A1 | 3/1988 | A61M 1/36 |
| EP | 0 578 086 | A1 | 1/1994 | A61M 1/36 |
| EP | 0 619 145 | A2 | 10/1994 | B04B 9/12 |
| EP | 0 664 159 | A1 | 7/1995 | B04B 5/04 |
| EP | 0 799 645 | A1 | 10/1997 | B04B 5/04 |
| EP | 0 885 619 | A1 | 12/1998 | A61M 1/36 |
| EP | 1 057 534 | A1 | 12/2000 | B04B 5/04 |
| EP | 1 295 619 | A2 | 3/2003 | A61M 1/38 |
| EP | 0 654 277 | A1 | 5/2005 | A61M 1/36 |
| FR | 2 258 898 | A1 | 8/1975 | B04B 1/00 |
| GB | 2 047 110 | A | 11/1980 | A61M 1/03 |
| JP | 59-006952 | A | 1/1984 | B04B 5/00 |
| JP | 59-069166 | A | 4/1984 | B04B 11/00 |
| JP | 61-502516 | A | 11/1986 | A61M 1/02 |
| JP | 02-052665 | A | 2/1990 | A61M 1/02 |
| JP | 03-131268 | A | 6/1991 | A61M 1/30 |
| JP | 07-075746 | B2 | 3/1995 | B21D 51/26 |
| JP | 8-500252 | A | 1/1996 | A61M 1/14 |
| JP | 08-131539 | A | 5/1996 | A61M 1/02 |
| JP | 09-192215 | A | 7/1997 | A61M 1/02 |
| SU | 660718 | A1 | 5/1979 | B04B 5/00 |
| SU | 762982 | A1 | 9/1980 | B04B 5/04 |
| SU | 1146098 | A | 3/1985 | B04B 5/00 |
| WO | WO 85/02561 | A1 | 6/1985 | B04B 1/10 |
| WO | WO 86/00231 | A1 | 1/1986 | A61M 1/03 |
| WO | WO 90/00059 | A1 | 1/1990 | A61K 35/14 |
| WO | WO 90/07383 | A1 | 7/1990 | B04B 7/08 |
| WO | WO 93/18324 | | 9/1993 | F16K 7/07 |
| WO | WO 94/06535 | A1 | 3/1994 | B01D 33/00 |
| WO | WO 96/11747 | A2 | 4/1996 | B04B 5/04 |
| WO | WO 96/33023 | A1 | 10/1996 | B04B 5/04 |
| WO | WO 02/05059 | A2 | 1/2002 | |

OTHER PUBLICATIONS

The State Intellectual Property Office of the People's Republic of China, First Official Action—Application No. 2009801197813, dated Nov. 26, 2012 (8 pages).

The State Intellectual Property Office of the People's Republic of China, First Official Action (Notification of the First Office Action)—Application No. 2009801197813, dated Nov. 26, 2012 (10 pages) [English Translation].

The State Intellectual Property Office of the People's Republic of China, Second Official Action—Application No. 200980119781.3, dated Oct. 15, 2013 (9 pages).

The State Intellectual Property Office of the People's Republic of China, Second Official Action (Notification of the Second Office Action)—Application No. 200980119781.3, dated Oct. 15, 2013 (13 pages) [English Translation].

Japanese Patent Office, First Official Action—Application No. 2011-504,203, dated Jun. 4, 2013 (3 pages).

Japanese Patent Office, First Official Action (Notification of Reason for Rejection)—Application No. 2011-504,203, dated Jun. 4, 2013 (4 pages) [English Translation].

Japanese Patent Office, Final Office Action (Final Decision for Rejection)—Application No. 2011-504,203, dated Oct. 8, 2013 (2 pages).

Japanese Patent Office, Final Office Action (Final Decision for Rejection)—Application No. 2011-504,203, dated Oct. 8, 2013 (2 pages) [English Translation].

Japanese Patent Office, First Official Action—Application No. 2014-19,951, dated Jan. 6, 2015 (2 pages).

Japanese Patent Office, First Official Action (Notification of Reasons for Rejection)—Application No. 2014-19,951, dated Jan. 6, 2015 (3 pages) [English Translation].

Japanese Patent Office, Second Official Action—Application No. 2014-19,951, dated Apr. 28, 2015 (2 pages).

Japanese Patent Office, Second Official Action—Application No. 2014-19,951, dated Apr. 28, 2015 (2 pages) [English Translation].

* cited by examiner

US 9,364,600 B2

SYSTEM AND METHOD FOR OPTIMIZED APHERESIS DRAW AND RETURN

PRIORITY

This application claims priority from and is a divisional application of co-pending U.S. patent application Ser. No. 13/076,882, entitled, "System and Method for Optimized Apheresis Draw and Return," filed on Mar. 31, 2011, and naming Etienne Pages and Michael Ragusa as inventors. U.S. application Ser. No. 13/076,882 claims priority from and is a divisional application of U.S. patent application Ser. No. 12/102,427, entitled, "System and Method for Optimized Apheresis Draw and Return," filed on Apr. 14, 2008, and naming Etienne Pages and Michael Ragusa as inventors. The disclosures of each of these applications are incorporated herein, in entirety, by reference.

TECHNICAL FIELD

The present invention relates to systems and methods for blood apheresis and particularly to systems and methods for optimized apheresis draw and return.

BACKGROUND ART

Apheresis is a procedure in which an individual blood component can be separated and collected from whole blood withdrawn from a subject. Typically, whole blood is withdrawn through a needle inserted into the subject's arm and transferred into a cell separator, such as a centrifugal bowl. Once the whole blood is separated into its various components (e.g., plasma, red blood cells, and platelets), one or more of the components can be collected from the centrifugal bowl. The remaining components can be returned to the subject along with a compensation fluid to make up for the volume of the removed component.

While performing apheresis procedures, the technician must balance the procedure time with the safety of the patient. In particular, the technician must perform the procedure as quickly as possible to minimize the procedure time and associated discomfort of the subject, but must always be conscious of the safety of the subject. One such area for safety concern is the pressure at which the whole blood is withdrawn from the subject and the remaining blood components are returned to the subject. The pressure at which the remaining components and potential compensation fluid are returned to the subject is critical to the safety of the subject. If the pressure is too high during the return or too low in during the draw, the subject is at risk for vein lesions.

To control the pressure of the blood withdrawn from and components returned to the subject, current systems attempt to measure a venous pressure. However, current systems typically measure the pressure within the line at a distance away from the access site. This distance creates inaccuracies in the measurement and, as a result, current systems can not accurately measure the venous pressure. As one can imagine, these inaccuracies increase the risk to the patient and, perhaps, force the technician to operate the apheresis system at a non-optimized rate. Despite measuring as close as possible to the venipuncture, current systems do not factor in the loss of pressure that occurs between the point of measure and the tip of the needle,

SUMMARY OF THE INVENTION

Embodiments of the present invention precisely determine donor vein pressure without the need for a sensor to be located within the vein. In some embodiments, pressure may be measured at two points within the line or lines that fluidly connect the needle tip to the apheresis device. The two measurement points (P1 and P2) may be located a distance away from the needle tip within the donor vein. The measurement points may delimit two portions of a line(s) having a known fluid resistance R1 and R2. R may be defined as the change in pressure between the two pressure measurement points divided by a flow rate and may be expressed in mmHg/ml/min. The two portions may include the portion of the line between the needle tip and the first point of measurement and the portion between the first and the second points of measurement. The vein pressure may be determined as a function of the measured pressures and the resistances within the line portions (e.g., Pv=f(P1, P2, R1, R2)) independently from the fluid characteristics and flow rate. Additionally, in some embodiments, Pv, P1 and P2 may be functions of time or of volume processed over time.

In accordance with embodiments of the present invention, a blood processing device for collecting and exchanging blood components includes a venous-access device for drawing whole blood from a subject and returning unused/uncollected blood components and potential compensation fluid to the subject, and a blood component separation device. The blood component separation device (e.g., a centrifuge bowl) separates the drawn whole blood into a first blood component and a second blood component. The blood component separation device may also send the second blood component to a second blood component storage container.

The blood processing device may also have a return line fluidly connecting the venous-access device and the blood component separation device. The system may use the return line to return the first blood component to the subject. The system may also have a first and second pressure sensor located on the return line. The first pressure sensor may be located between the blood component separation device and the venous-access device and may determine a first pressure within the return line. The second pressure sensor may be located between the first pressure sensor and the venous-access device and may determine a second pressure within the return line. A pump connected to the return line may control a return flow rate within the return line based on a subject access pressure determined using the first pressure and the second pressure. The subject access pressure may be determined in real time.

In accordance with other embodiments, the system may also have an anticoagulation line for introducing anticoagulant into the drawn blood near the venous-access device. Additionally, the system may include a valve, located on the return line between the blood component separation device and the venous access device. The valve may stop the flow within the return line. The system may also have an interlock that stops the withdrawal of whole blood from the subject when the system is returning the first blood component to the subject.

In still other embodiments, the subject access pressure may also be based on at least one characteristic of a first portion of the return line and at least one characteristic of a second portion of the return line. The first portion may be between the first and second pressure sensors. The second portion may be between the second pressure sensor and the venous-access device. The characteristics of the first and second portions of the return line may include, but are not limited to, the length, inner diameter, resistance to flow, and materials of construction. The system may also control the return flow rate based on the flow resistances within the first and second portions of the return line. The flow resistances may be calculated based on the line characteristics discussed above.

In accordance with still further embodiments of the present invention the blood component separation device may further separate the drawn blood into a third blood component in addition to the first blood component and the second blood component. The first blood component may be red blood cells, the second blood component may be platelets, and the third blood component may be plasma.

In accordance with other embodiments of the present invention, a method of collecting and exchanging blood components using blood processing equipment includes inserting a venous-access device into a subject, and withdrawing whole blood from the subject. The venous-access device may be fluidly connected to a blood separation device in which the drawn blood is collected. The method then separates the withdrawn blood into a first blood component and a second blood component using the blood component separation device, and extracts the second blood component from the blood component separation device. The system or method may return the remaining components (e.g., the first blood component) to the subject through a return line.

In some embodiments, the method may measure a first pressure within the return line using a first pressure sensor, and a second pressure within the return line using a second pressure sensor. The first and second pressure sensors may be located on the return line. For instance, the first pressure sensor may be located on the return line between the venous-access device and the blood component separation device, and the second pressure sensor may be located on the return line between the venous-access device and the first pressure sensor. The method may then control a return flow rate within the return fluid line based on a subject access pressure that is determined using the first pressure and the second pressure.

In accordance with further embodiments, the subject access pressure may also be determined using at least one characteristic of a first portion of the return line and at least one characteristic of a second portion of the return line. The first portion is between the first and second pressure sensors, and the second portion is between the second pressure sensor and the venous-access device. The characteristics of the line portions can include the length, inner diameter, and materials of construction. The flow rate may also be controlled based on a first flow resistance within the first and/or second portion of the return line. The flow resistances may be calculated based on the characteristics of the respective portion of the return line.

In accordance with still further embodiments of the present invention, the blood component separation device further separates the drawn blood into a third blood component in addition to the first blood component and the second blood component. The first blood component may be platelets, the second blood component may be red blood cells, and the third blood component may be plasma. In some embodiments, the subject access pressure is determined in real-time.

In accordance with other embodiments of the present invention, a blood processing device for collecting and exchanging blood components may include a venous-access device and a blood component separation device. The device may utilize the venous access device to draw whole blood from a subject and return unused blood components to the subject. The blood component separation device may separate the drawn whole blood into a first blood component and a second blood component, and send the second blood component to a second blood component storage container.

The blood processing device may also have a return line and a draw line. The return line fluidly connects the venous-access device and the blood component separation device and may be used to return the first blood component to the subject. The draw line also fluidly connects the venous-access device and the blood component separation device and may be used to draw whole blood from the subject and into the blood component separation device The blood processing device may also have a first pressure sensor located on the return line and a second pressure sensor located on the draw line. Each of the sensors may be located between the blood component separation device and the venous-access device on their respective lines and may measure a pressure. A pump, connected to the return line, may control the return flow rate based on a subject access pressure determined based on the pressures measured by the sensors.

In accordance with other embodiments, a method of collecting and exchanging blood components using blood processing equipment may include inserting a venous-access device into a subject and withdrawing blood from the subject through a draw line. The method may then separate the withdrawn blood into a first blood component and a second blood component using a blood component separation device. Once the blood is separated into components, the method may extract the second blood component from the blood component separation device and return the first blood component to the subject through a return line.

The method may also measure a first pressure and a second pressure using a first sensor and a second sensor, respectively. The first pressure sensor may be located on the return line between the venous-access device and the blood component separation device. The second pressure sensor may be located on the draw line between the venous-access device and the blood component separation device. The method may then control a flow rate based on a subject access pressure determined using the first pressure and the second pressure.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Embodiments of the present invention provide a system and method for performing a blood apheresis procedure. Specific embodiments of the present invention optimize the withdrawal of whole blood from a subject and the return of unharvested or processed blood component to the subject. The method and system may use multiple pressure sensors on the withdraw and/or return line to determine the pressure at the subject access site, and control the flow of fluids within the system based on this pressure. Details of illustrative embodiments are discussed below.

Figure 1A:
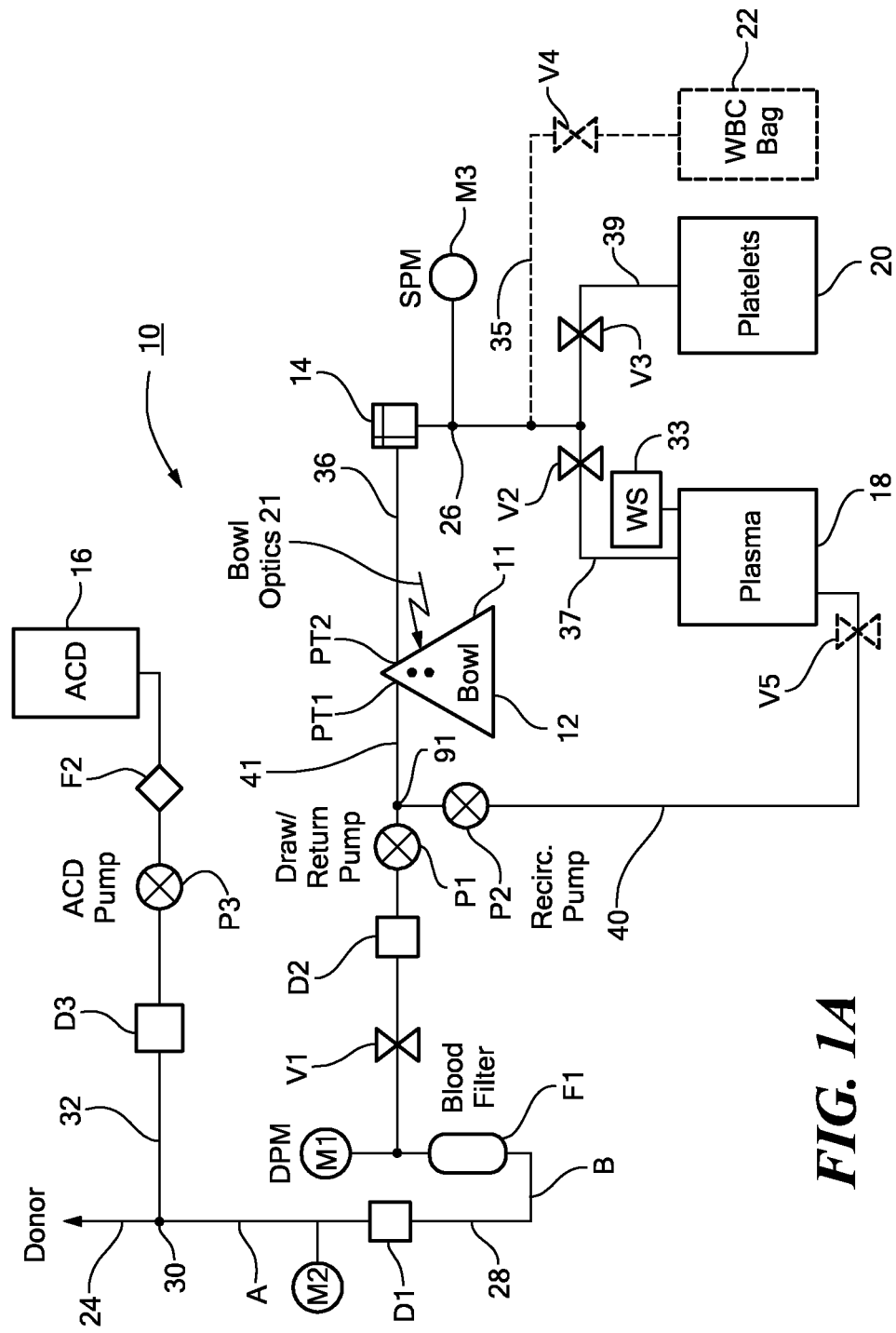
FIG. 1A shows a schematic diagram of an apheresis system in accordance with embodiments of the present invention.
Figure 2:
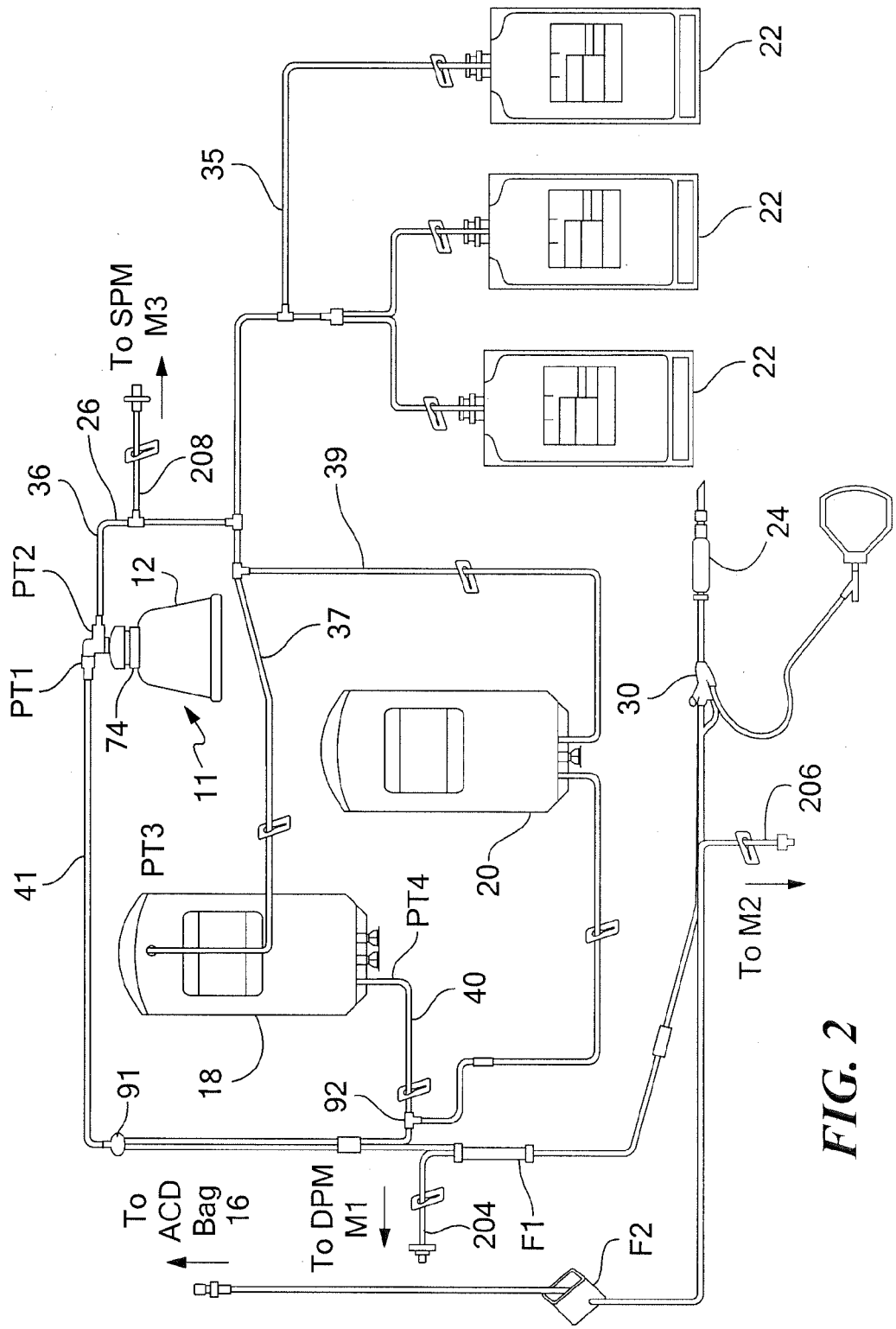
FIG. 2 schematically shows a disposable system for use with the apheresis system of FIG. 1A, in accordance with one embodiment of the present invention.

As shown in FIGS. 1A and 2, and as mentioned above, an apheresis system 10, in accordance with embodiments of the present invention, withdraws whole blood from a subject through a venous access device 24 using a withdraw pump P1. The venous access device 24 can be any number of devices capable of accessing a subject's veins including, but not limited to a phlebotomy needle. As the system 10 withdraws the whole blood from the subject, the blood passes through a draw/return line 28 and enters a blood component separation device 11, such as a standard Latham type centrifuge. The blood component separation device 11 separates the whole blood into its constituent components (e.g., red blood cells, white blood cell, plasma, and platelets). Although a Latham type centrifuge is mentioned above, other types of separation chambers and devices may be used, such as, without limitation, an integral blow-molded centrifuge bowl, as described in U.S. Pat. Nos. 4,983,156 and 4,943,273, which are hereby incorporated by reference.

As the system 10 withdraws the whole blood from the subject, the system 10 may introduce anticoagulant into the withdrawn whole blood to prevent the blood from coagulating within the lines or within the blood component separation device 11. To that end, the system 10 may include an anticoagulant line 32 fluidly connected to an anticoagulant source 16 (e.g., a bag of anticoagulant) at one end, and the venous-access device 24 (or the draw/return line 28 via a y-connector 30) at the other end. An anti-coagulant pump P3, through which the anticoagulant line 32 passes, may control the flow of anticoagulant within the anti-coagulant line 32 and the amount of anticoagulant introduced into the whole blood. Although the anticoagulant can be added to the whole blood at any point, it is preferred that the anticoagulant be introduced as close as possible to the venous-access device 24.

The anticoagulant line 32 may also include a bacteria filter F2 that prevents any bacteria in the anticoagulant source 16, the anticoagulant, or the anticoagulant line 32 from entering the system 10 and/or the subject. Additionally, the anticoagulant line 32 may include an air detector D3 that detects the presence of air within the anticoagulant. The presence of air bubbles within any of the system 10 lines can be problematic for the operation the system 10 and may also be harmful to the subject if the air bubbles enter the blood stream. Therefore, the air detector D3 may be connected to an interlock that stops the flow within the anticoagulant line 32 in the event that an air bubble is detected (e.g., by stopping the anticoagulant pump P3 or closing a valve on the anticoagulant line 32), thereby preventing the air bubbles from entering the subject.

Once a desired amount of anti-coagulated whole blood is withdrawn from the subject and contained within the blood component separation device 11, the blood component separation device 11 separates the whole blood into several blood components. For example, the blood component separation device 11 may separate the whole blood into a first, second, third, and, perhaps, fourth blood component. More specifically, the blood component separation device 150 can separate the whole blood into plasma, platelets, red blood cells, and, perhaps, white blood cells.

Figure 3:
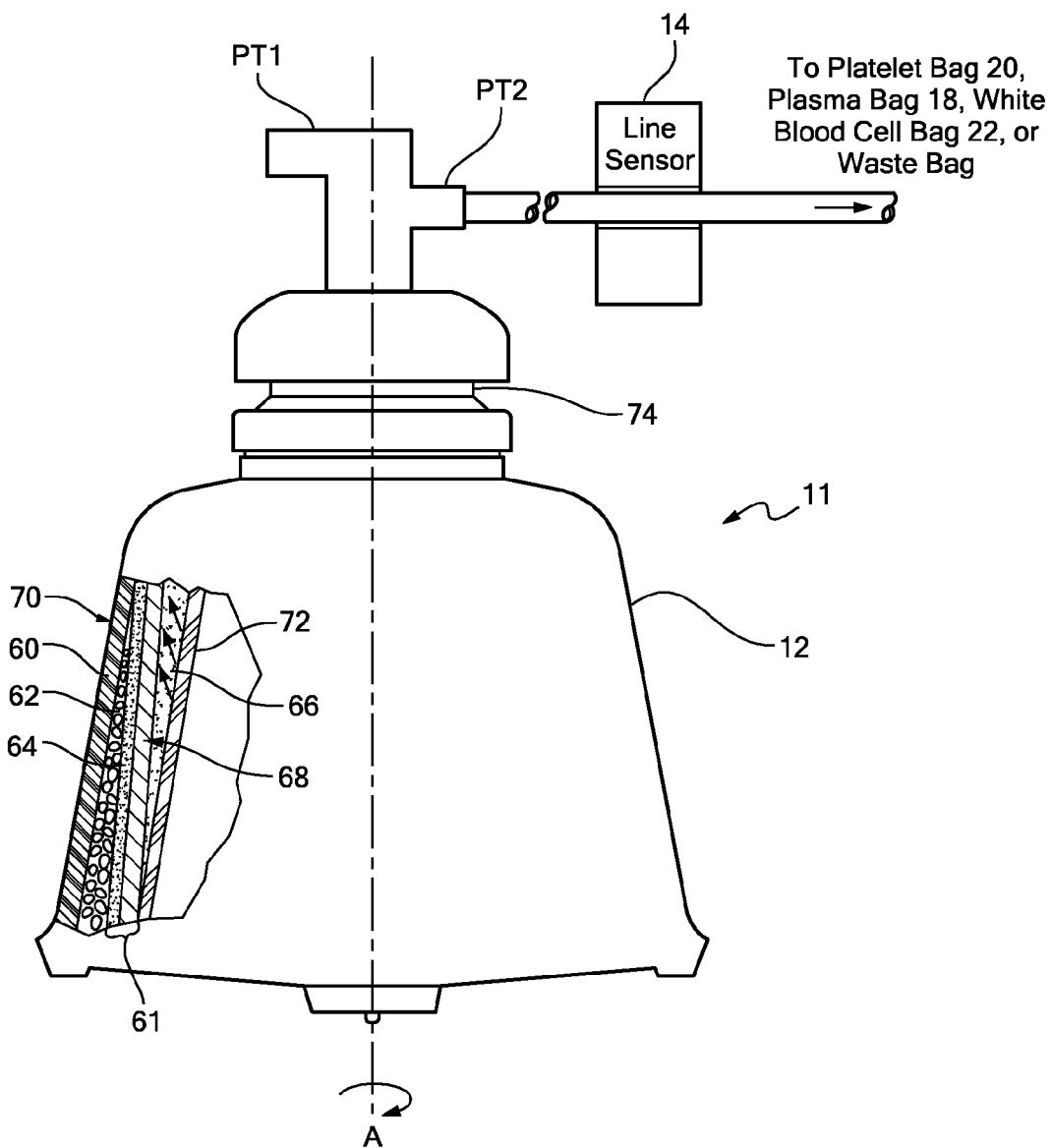
FIG. 3 schematically shows a side view of a blood component separation device for use with the apheresis system of FIG. 1A, in accordance with embodiments of the present invention.

As shown in FIG. 3, when a Latham centrifuge is used, the blood component separation device 11 includes a rotatable bowl 12 and stationary input and output ports PT1 and PT2 fluidly coupled to the bowl interior by a rotary seal 74. The draw/return line 28 fluidly connects the venous access devices 24 (e.g., the phlebotomy needle) and the input port PT1. In some embodiments, the venous access device 24 may be replaced with a whole blood bag (not shown) in case the whole blood is to be first pooled and then supplied. In such embodiments, the draw line 28 will fluidly connect the whole blood bag with the input port PT1.

As mentioned above, the blood component separation device 11 separates the whole blood into its constituent components. In particular, as the bowl 12 rotates, centrifugal forces separate the anticoagulated whole blood admitted into the bottom of the bowl into red blood cells (RBC), white blood cells (WBC), platelets and plasma. The number of rotations of the bowl 12 can be selected, for example, within a range of 4,000 to 6,000 rpm, and is typically 4,800 rpm. The blood is separated into different fractions in accordance with the component densities. The higher density component, i.e., RBC 60, is forced to the outer wall 70 of the bowl 12 while the lower density plasma 66 lies nearer the core 72. A buffy coat 61 is formed between the plasma 66 and the RBC 60. The buffy coat 61 is made up of an inner layer of platelets 64, a transitional layer 68 of platelets and WBC and an outer layer of WBC 62. The plasma 66 is the component closest to the outlet port from the separation region and is the first fluid component displaced from the bowl 12 via the outlet port PT2 as additional anticoagulated whole blood enters the bowl 12 through the inlet port PT1.

The system 10 may also include an optical sensor 21 that may be applied to a shoulder portion of the bowl 12. The optical sensor 21 monitors each layer of the blood components as they gradually and coaxially advance toward the core 72 from the outer wall 70 of the bowl 12. The optical sensor 21 may be mounted in a position at which it can detect the buffy coat reaching a particular radius, and the steps of drawing the whole blood from the donor 401 and introducing the whole blood into the bowl 402 may be terminated in response to the detection.

Once the blood component separation device 11 has separated the blood into the various components, one or more of the components can be removed from the blood component separation device 11. For instance, the plasma may be removed to a plasma bag 18 through line 37 (FIG. 1A and FIG. 2) or a waste bag (not shown). Alternatively, the plasma may be removed to a plasma reservoir (not shown) located on the draw/return line 28, or the white blood cells (WBC) may be removed to one or more white blood cell bags 22 via line 35. Some embodiments of the system 10 may include a weight sensor 33 that measures the amount plasma collected. Although not shown, the platelet bag 20 and the white blood cell bag 22 may include similar weight sensors. The removed plasma may be later reintroduced into the blood component separation device 11 via line 40 and recirculation pump P2 at an increasing rate to extract and send the platelets to a platelet bag 20 via line 39. This process is known as surge elutriation.

In some embodiments, the system 10 may also include a line sensor 14 that can determine the type of fluid (e.g., plasma, platelets, red blood cells etc.) exiting the blood component separation device. In particular, the line sensor 14 consists of an LED which emits light through the blood components leaving the bowl 12 and a photo detector which receives the light after it passes through the components. The amount of light received by the photo detector is correlated to the density of the fluid passing through the line. For example, if plasma is exiting the bowl 12, the line sensor 14 will be able to detect when the plasma exiting the bowl 12 becomes cloudy with platelets (e.g., the fluid existing the bowl 12 is changing from plasma to platelets). The system 10 may then use this information to either stop the removal of blood components from the bowl 12 or redirect the flow by, for example, closing valve V2 and opening valve V3.

Once the system removes the desired components from the blood component separation device 11, the system 10 can return the remaining components to the subject. The system may use the draw/return pump P1 to return the components to the subject via the draw/return line 28, which, as mentioned above, fluidly connects the blood component separation device 11 and the venous-access device 24. Alternatively, if the system 11 is so equipped, the system may return the components to the subject via a dedicated return line 27, FIG. 1B. Like the anticoagulant line 32 and the draw/return line 28, the dedicated return line 27 may also have a dedicated return pump P5 that controls the direction, rate, and duration of the fluid flow within the return line. In such embodiments, the return line 27 also fluidly connects to the venous-access device 24, preferably at a point between the return pump P5 and the venous-access device 24. Additionally, in such embodiments, the system 10 will also have a dedicated draw line 29 and draw pump P4. In some embodiments, the system 10 may include an interlock that stops the withdrawal of whole blood from the subject when the system is returning the first blood component to the subject.

As shown in FIG. 1A and as mentioned briefly above, the system 10 can have a plurality of valves located through-out the system to control the flow of fluid within the system 10. For example, draw/return line 28 may contain a valve V1 that allows flow through the lines when open and prevents flow when closed. Additionally, the lines 35, 37 and 39 leading to the white blood cell, plasma and platelet bags, respectively may have at least one valve V2, V3, V4, and V5 (e.g., line 37 has a valve V2 at the inlet of the plasma bag 18 and a valve V5 at the outlet of the plasma bag 18, and line 39 has a valve V3 at the inlet of the platelet bag 20). Additionally, the inlet to the blood component separation device 11 may have valves (not shown) that either allow or prevent flow to or from the blood component separation device 11. Any of the above mentioned valves can be either manual or automatic. In other words, the valves may be manually operated by the user/technician or can be automatically operated, for example, by a controller, when a particular condition is met (e.g., closing valve V1 when air is detected in the draw/return line 28, as discussed below).

Like the anticoagulant line 32, the draw/return line 28 can also include a number of sensors, filters, and detectors to ensure the safety of the subject and an optimized system operation. In particular, as shown in FIG. 1A, the draw/return line 28 may include air detectors D1 and D2 to detect the presence (or absence) of air within the line 28. The air detectors D1 and D2 can be connected to an interlock that, when the detectors D1 and D2 detect air, stops flow within the draw/return line 28 (e.g., by stopping the draw/return pump P1 or closing valve V1). Additionally, the draw line 28 can include a blood filter F1 that removes any bacteria, contamination, or particulates that may be present in the withdrawn blood or the returning components. The system 10 may also include a system pressure monitor (SPM) M3 that monitors pressure levels within the system 10. Like the first and second pressure monitors M1 and M2, discussed in greater detail below, the system pressure monitor M3 can include a sample line 208 (FIG. 2) connected to line 36 (e.g., the line leading from the outlet of the blood component separation device 11).

As mentioned above, the pressure and flow rate at which the system withdraws blood from the subject and the rate at which the system returns unharvested components to the subject are critical not only to the overall time and efficiency of the procedure, but also the safety of the subject. If the pressure and flow rate are too low, the procedure will take longer than needed, thus increasing the subject's discomfort. However, if the pressure and flow rate are too high, the subject may encounter problems such as vein lesions. To that end, embodiments of the present invention include pressure monitors M1 and M2 that monitor the pressure within the draw/return line 28 (or dedicated return line 27 and dedicated draw line 29)

Unlike prior art systems that monitor the return pressure only at a single point, embodiments of the present invention, as mentioned above, monitor the return pressure at two locations. In some embodiments, the system 10 can use the pressure measurements from pressure sensors M1 and M2 to control the flow rate and maintain the pressures within a desired range. Additionally or alternatively, the system 10 may also use this pressure information to obtain an accurate measure of the pressure at the venous access device 24 (e.g., the subject access pressure).

In embodiments having a shared draw/return line 28, the first pressure sensor M1 may be located on the draw/return line 28 between the venous access device 24 and the blood component separation device 11. The second pressure sensor M2 may be located between the venous access device 24 and the first pressure sensor M1. The first and second pressure sensors M1 and M2 can either be located directly on the draw/return line 28, or they may be connected to the draw/return line 28 via sample lines 204 and 206, respectively. The system 10 can then use the pressure measurements from M1 and M2 and the characteristics (e.g., length, inner diameter, constitutive materials, etc.) of portion A of the draw/return line 28 (e.g., the portion between the venous access device 24 and the second pressure sensor M2) and portion B of the draw/return line 28 (e.g., the portion between the pressure sensors M1 and M2) to calculate the subject access pressure. In particular, the system 10 may use the known characteristics of the line portions A and B to calculate the resistances of each portion. Because the line characteristics are known prior to the start of processing, the system and or operating technician can calculate the resistances in advance.

The system may then calculate, in real-time, the subject access pressure according to the equations described in greater detail below. It is important to note that the equation used by the system is dependent upon whether the system is performing a draw step or a return step.

For example, during a draw step, the system may use the following equation:

$$P_v = P_{M2} - P_{HM2} + (R_A/R_B)*((P_{M2}-PH_{M2})-(P_{M1}-PH_{M1}))$$

Conversely, during the return step, the system may use the following equation:

$$P_v = P_{M2} - P_{HM2} - (R_A/R_B)*((P_{M1}-P_{HM1})-(P_{M2}-P_{HM2}))$$

Where, $R_A$=the resistance to flow in tubing section A (e.g., including the needle, needle line, and draw/return line 28 to sensor M2;

$R_B$=the resistance to flow in tubing section B (e.g., including the draw/return line 28 between sensors M1 and M2); and $P_{HM1}$ and $P_{HM2}$=the part of $P_{M1}$ and $P_{M2}$, respectively, that is associated with the difference in height between the venous access device 24 and the pressure sensors M1 and M2.

Figure 1B:
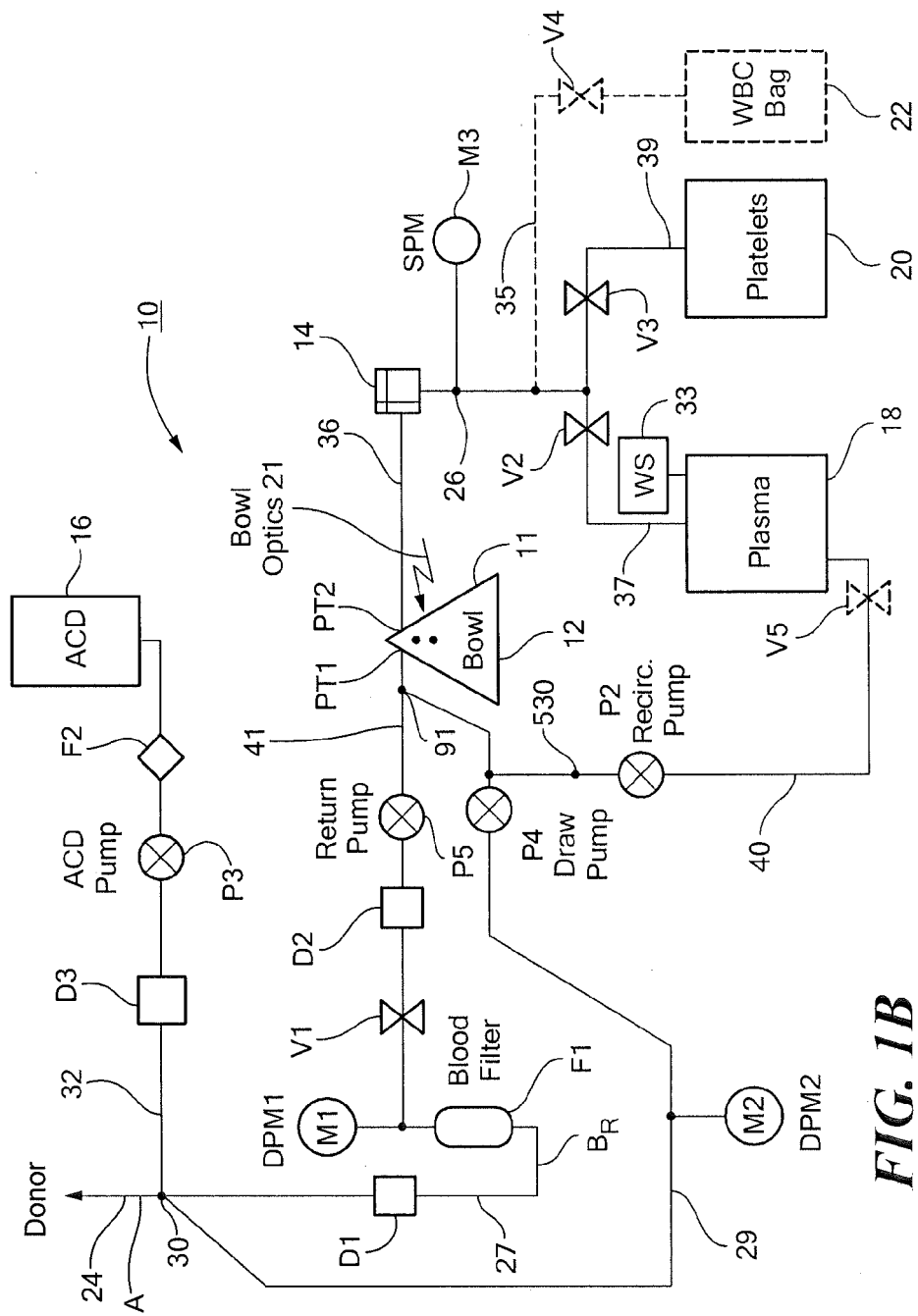
FIG. 1B shows a schematic diagram of an alternative embodiment of an apheresis system in accordance with embodiments of the present invention.
Figure 1C:
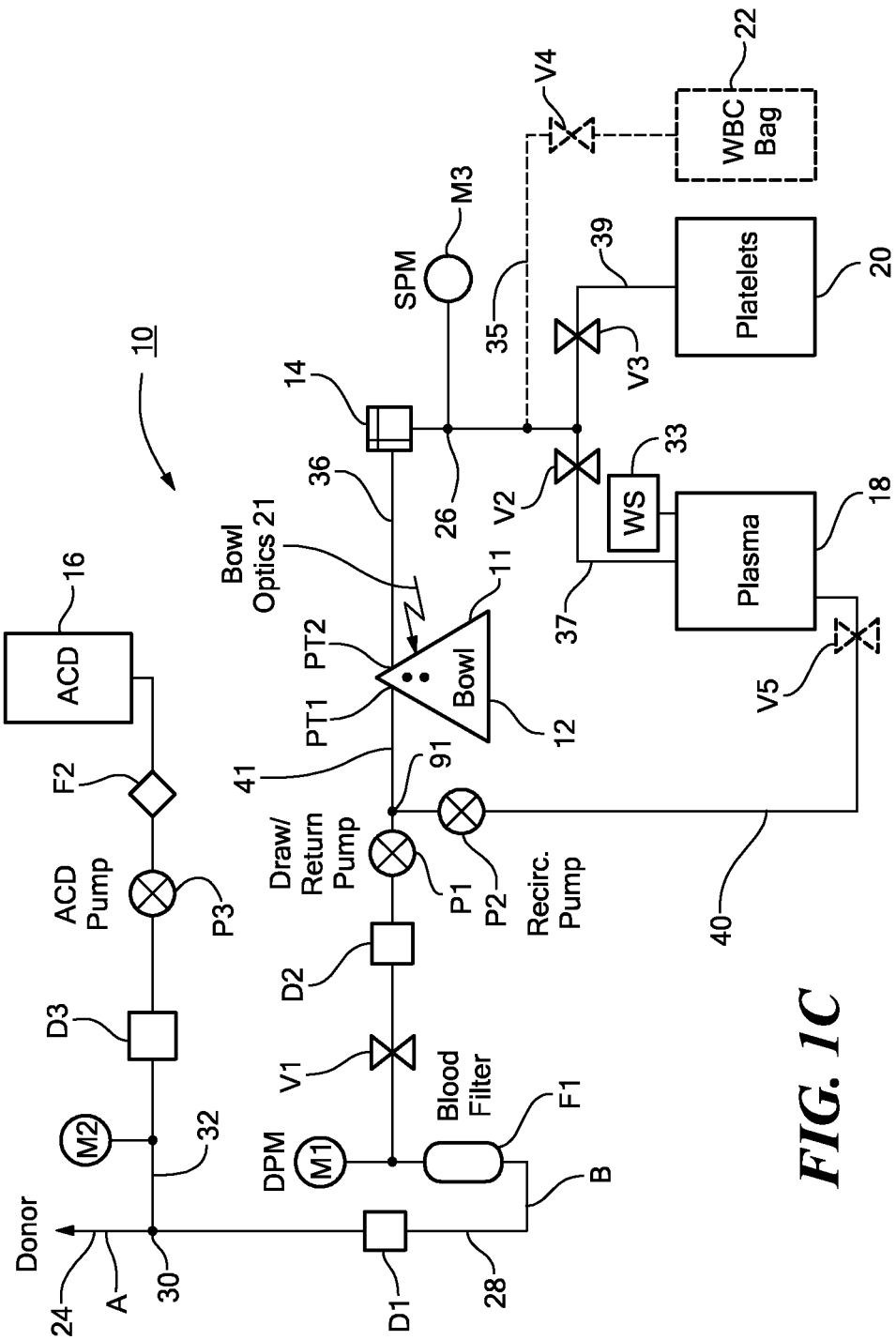
FIG. 1C shows a schematic diagram of an additional alternative embodiment of an apheresis system in accordance with embodiments of the present invention.

Although the pressure sensors M1 and M2 are described above as being located on the same line (e.g., the draw/return line 28), the pressure sensors M1 and M2 can be located on different lines. For example, as shown in FIG. 1B, if the system 10 has a dedicated draw line 29 with a draw pump P4 and a dedicated return line 27 with a return pump P5 (as discussed above), the pressure sensors M1 and M2 may be located on separate lines. For example, pressure sensor M1 may be located on the return line 27 and pressure sensor M2 may be located on the draw line 29. In such embodiments, portion A is located between the venous access device 24 and connector 30. However, the location of portion B is dependent on whether the subject access pressure is being determined for a draw step or a return step. In particular, during a draw step portion B (shown as $B_D$ on FIG. 1B) is located between connector 30 and pressure sensor M2. Alternatively, during the return step, portion B (shown as $B_R$ on FIG. 1B) is located between connector 30 and pressure sensor M1.

In addition to changing the location of the portions A and B and the location of the pressure sensors M1 and M2, systems having a dedicated return line 27 and dedicated draw line 29 must also utilize different equations to determine the subject access pressure. Additionally, in a similar manner to the systems having only the draw/return line 28, the equations used by the system are dependant upon whether the system is performing a draw step or a return step. For example, during the draw step, the system can determine the subject access pressure according to the following equation:

$$P_V = P_{M1} - P_{HM1} + r_D/R_D * [(P_{M1} - P_{HM1}) - (P_{M2} - P_{HM2})],$$
where R is the resistance to flow of the donor line (e.g., portion $B_D$),
r is the resistance to flow of the needle and the needle tubing (e.g., portion A), and
$P_{HM2}$ and $P_{HM1}$ respectively stand for the part of $P_{M2}$ and $P_{M1}$ that is associated with the difference in height between the vein puncture and the pressure sensors.

Conversely, during the return step, the system can determine the subject access pressure according to the following equation:

$$P_V = P_{M2} - P_{HM2} - r_R/R_R * [(P_{M1} - P_{HM1}) - (P_{M2} - P_{HM2})]$$
where R is the resistance to flow of the donor line (e.g., portion $B_R$),
r is the resistance to flow of the needle and the needle tubing (e.g., portion A), and
$P_{HM2}$ and $P_{HM1}$ respectively stand for the part of $P_{M2}$ and $P_{M1}$ that is associated with the difference in height between the vein puncture and the pressure sensors.

It is important to note that the above equations may be used when certain conditions are met for correcting $P_{DPM2}$ for the loss of pressure that occurs in the needle and the needle tubing (e.g., the portion of the tubing located between the needle tip and connector 30). In particular, the conditions are met when (1) the disposable set is known such that the resistances r and R are known, (2) the needle resistance r or the ration of r/R are not the same in the draw and the return steps, (3) the overall donor line (e.g., the DPM1 and DPM2 lines) is full with fluid that may be considered to have a homogenous viscosity, and (4) the relative positions of the venous access device 24 and the pressure sensors M1 and M2 are known so as to define $P_{HDPM1}$ and $P_{HDPM2}$.

It is important to note that during the draw process, there is generally no need to account for any differences in fluid viscosities. In particular, this is because the nature of processed fluid during draw is always whole blood or anticoagulated whole blood. Therefore, condition (3), mentioned above, is generally met. However, during the return process, the fluid at the first pressure sensor (e.g., M1) may be different from that at the second pressure sensor (e.g., M2). For example, whole blood may be located at the first pressure sensor M1 and packed red blood cells may be located at the second pressure sensor. The difference in fluid at the pressure sensors may be caused any number of a variety of factors. For example, portions of the line near one of the sensors may contain fluid from a previous process (e.g., the draw process or a prior return process). Additionally or alternatively, the difference in fluid can arise as the characteristics of the fluid exiting the separation device change (e.g., as the fluid changes from one blood component to another). In either scenario, there is a period of time (e.g., the time required for the fluid to travel between the sensors) that the first sensor M1 and the second sensor M2 are seeing different fluids and, therefore potentially different viscosities.

In part because of the ability for real time determination of pressures, embodiments of the present invention are able to detect and compensate for fluid viscosity changes in the lines. For example, embodiments of the system may compensate for viscosity and fluid changes within the portion of line having resistance R by applying the changes to the portion of the line having resistance r. Under a mathematically simplified form, when the condition (3) is not met, the equation may become: $Pv(t) = P_{M2}(t) - P_{HM2} - r_R/R_R * [(P_{M1}(t-\Delta t) - P_{HM1}) - (P_{M2}(t-\Delta t) - P_{HM2})]/Flow(t-\Delta t) \times Flow(t)$, where $\Delta t$ can be broadly defined as the time needed for the fluid of changed viscosity to travel from the portion of line of resistance R to that of resistance r.

Accordingly, the system 10 is able to, in real-time, precisely measure the subject access pressure, without knowing the flow rate of the fluid within line 28 or the fluid viscosity. The system 10 may then control the flow rate through draw/return line 28 (or draw line 29 and return line 27) based on the pressure measurements from pressure sensors M1 and M2 or the calculated subject access pressure. By controlling the flow rate in this manner, the system 10 can maintain the pressure in a desired operating range. The operating range may be determined based on a number of factors including, but not limited to, the size of the venous access device 24, subject characteristics (age, height, weight, health, etc.), the location of the venous access device 24 (e.g., into which vein it is inserted), cuff pressure, and system characteristics. This allows the system to operate at an optimum flow rate (e.g., the flow rate at which the whole blood is withdrawn and the flow rate at which the components are returned to the subject), without exposing the subject to an increased risk of vein lesions or other complications.

As shown in FIGS. 1A-C and 2 and as discussed above, the system 10 includes a number of lines leading to and from each of the system components. In many instances, multiple lines lead into a single line. In such cases, the system 10 may include line connectors to connect the lines. The line connectors may be y-site connectors such as connector 30, which connects the anticoagulant line 32 with the draw/return line 28, and connector 91, which connects line 40 coming from the plasma bag 18 and the draw/return line 28 (the outlet of the y-connector is line 41 leading to PT1). Alternatively, the connectors can be T-site connectors such as connector 92, which connects the lines 37 and 39 with line 36, and connector 26 which connects the sample line 208 for system pressure monitor M2 with line 36.

Figure 4:
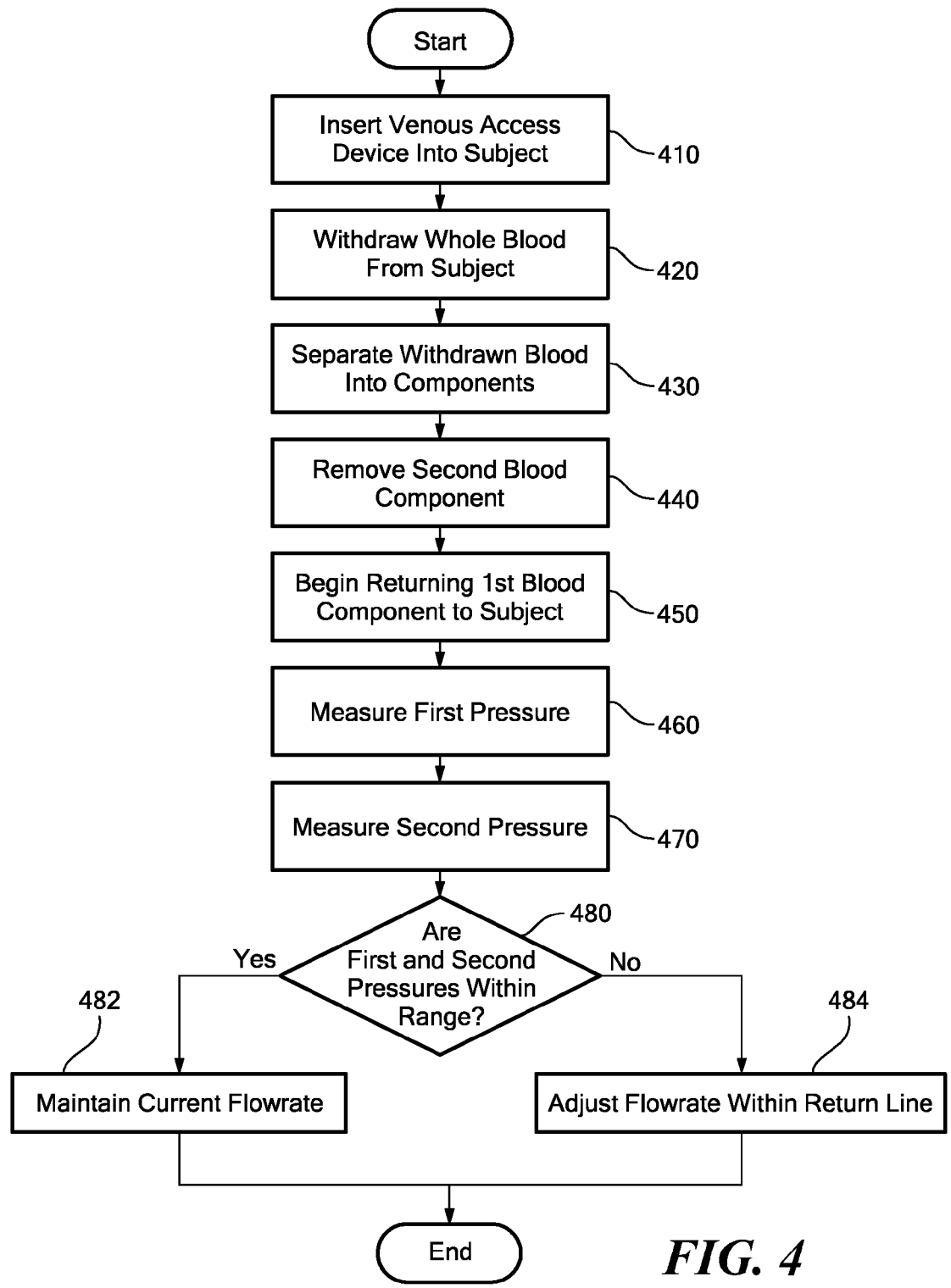
FIG. 4 shows a flowchart showing the steps of a method of using the apheresis system of FIG. 1A in accordance with one embodiment of the present invention.

FIG. 4 schematically shows a flowchart depicting a method of using the dual-pressure sensor apheresis system described above. In particular, the method first inserts the venous access device 24 into the subject (Step 410), and then begins to withdraw whole blood through the draw/return line 28 (or draw line 29) (Step 420). As mentioned above, draw pump P1 controls the direction, rate, and duration of the flow within the draw/return line 28. As the system 10 withdraws the whole blood from the subject, the anticoagulant pump P3 introduces anticoagulant from the anticoagulant source 16 into the whole blood via the anticoagulant line 32. As described above, the anticoagulant prevents the whole blood from coagulating within the system.

Once the anticoagulated whole blood reaches the blood component separation device 11, the blood component separation device 11 separates the blood into the constituent components (e.g., red blood cells, plasma, platelets, and white blood cells) in the layered orientation described above (Step 430). The technician operating the system may then extract one or more of the components (the component extracted is dependent on the purpose of the procedure) (Step 440) and return the remaining blood components to the subject (Step 450). As the method 10 returns the components to the subject, the method may also measure the pressure within draw/return line 28 (or return line 27) at two points using pressure sensors M1 and M2 (Steps 460 and 470). If the first and second pressures are within the appropriate range (Step 480), the system 10 is operating at a safe and optimized flow rate and the system 10 can maintain the current flow rate (Step 482). If the first and second pressures are outside of the desired range, the system can adjust the flow rate such that the pressure is within range (Step 484). For example, if the pressures are low, the system 10 can increase the flow rate (e.g., by increasing the speed of the draw pump P1) so that that flow rate is optimized. Alternatively, if the pressures are above the desired range, the system 10 can decrease the flow rate (e.g., by decreasing the speed of draw pump P1) so that the flow rate and pressures are safe for the subject.

Figure 5:
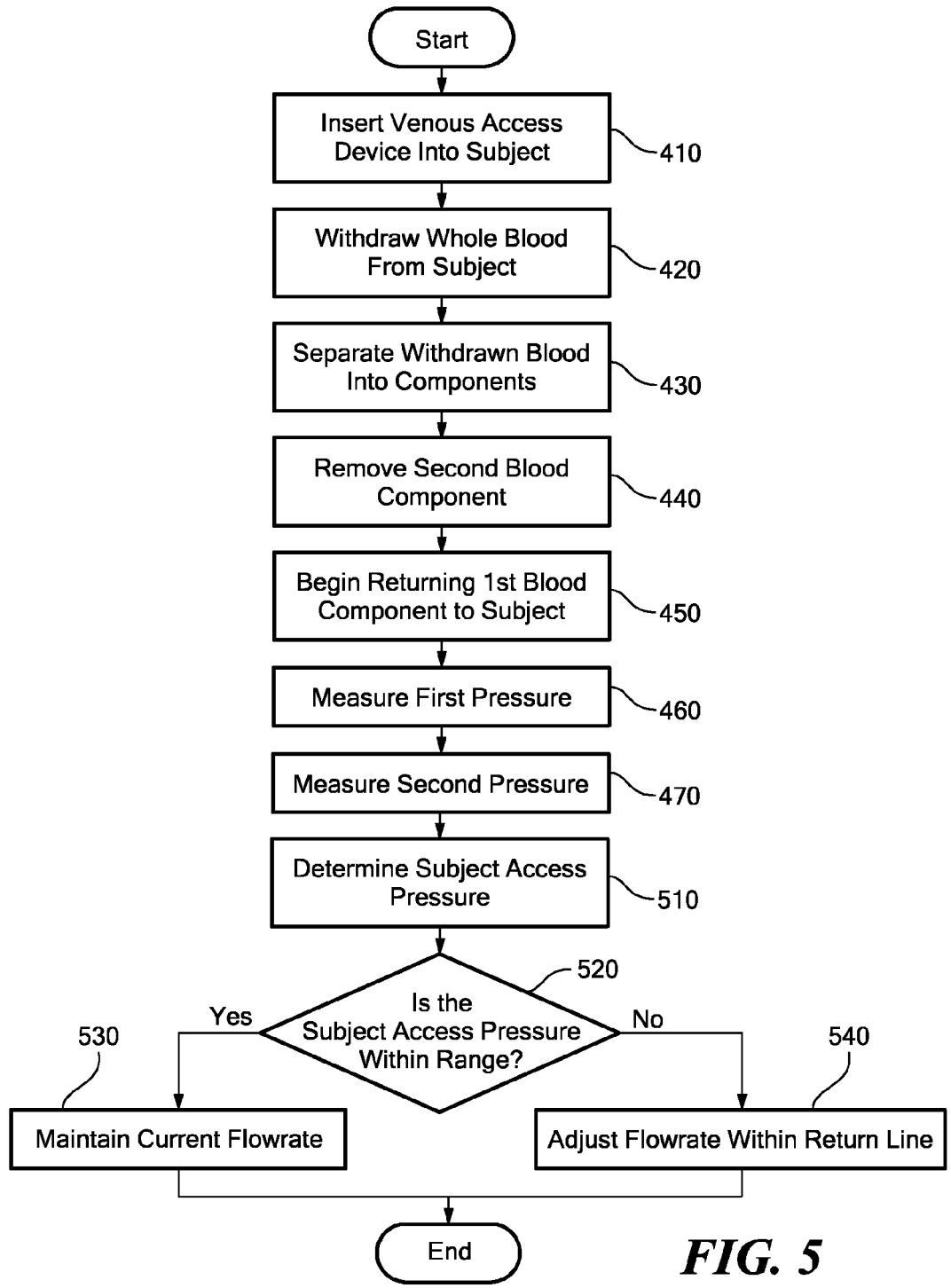
FIG. 5 shows a flowchart showing the steps of a second method of using the apheresis system of FIG. 1A in accordance with an additional embodiment of the present invention.

In accordance with other embodiments, and as shown in FIG. 5, the method of using the dual pressure apheresis may also include several additional, optional steps. In particular, after measuring the first pressure (Step 460) and the second pressure (Step 470), the system 10 may use the measured pressures to calculate the subject access pressure (Step 510), as described above. The method may then determine whether the subject access pressure is within a desired range (Step 520). If the subject access pressure is within range, the method can maintain the flow rate within the draw/return line 28 (or draw line 29 and return line 27) (Step 530) because it is safe for the subject and optimized. If the subject access pressure is outside of the range, the method can adjust the flow rate such that it is within range (Step 540). For example, if the pressures are low, the system 10 can increase the flow rate (e.g., by increasing the speed of the draw pump P1) so that that flow rate is optimized. Alternatively, if the pressures are above the desired range, the system 10 can decrease the flow rate (e.g., by decreasing the speed of draw pump P1) so that the flow rate and pressures are safe for the subject.

It should be noted that all of the components of the system should be made of suitable materials that are compatible with the substance with which they are in contact. For example, the draw/return line 28, draw line 29, return line 27, and lines 36, 37, and 40 should be compatible with blood and blood components. Additionally, the platelet bag 20 and the plasma bag 18 should be compatible with platelets and plasma, respectively. Likewise, the anticoagulant line 32 should be compatible with anticoagulant.

Although the above discussion discloses various exemplary embodiments of the invention, it should be apparent that those skilled in the art can make various modifications that will achieve some of the advantages of the invention without departing from the true scope of the invention.

We claim:

1. A method of collecting and exchanging blood components using blood processing equipment comprising:
    inserting a venous-access device into a subject, the venous-access device fluidly connected to a blood separation device;
    withdrawing blood from the subject such that the drawn blood is collected in a the blood component separation device for processing;
    separating the withdrawn blood into a first blood component and a second blood component using the blood component separation device;
    extracting the second blood component from the blood component separation device;
    returning the first blood component to the subject through a draw/return line;
    measuring a first pressure within the draw/return line using a first pressure sensor, the first pressure sensor being located on the draw/return line between the venous-access device and the blood component separation device;
    measuring a second pressure within the draw/return line using a second pressure sensor, the second pressure sensor being located on the draw/return line between the venous-access device and the first pressure sensor; and
    controlling a flow rate within the draw/return fluid line based on a subject access pressure determined using the first pressure and the second pressure.

2. A method according to claim 1 further including introducing anticoagulant into the withdrawn blood through an anticoagulant line.

3. A method according to claim 1, wherein the blood component separation device is a centrifuge bowl.

4. A method according to claim 1, wherein the draw/return line includes a valve located between the blood component separation device and the venous-access device, the valve stopping the flow within the draw/return line.

5. A method according to claim 1, wherein the subject access pressure is further determined using at least one characteristic of a first portion of the draw/return line and at least one characteristic of a second portion of the draw/return line, wherein the first portion is between the first and second pressure sensors and the second portion is between the second pressure sensor and the venous-access device.

6. A method according to claim 5, wherein the at least one characteristic of the first portion of the draw/return line and the at least one characteristic of the second portion of the draw/return line are selected from the group consisting of length, inner diameter, and materials of construction.

7. A method according to claim 5, wherein the flow rate is also controlled based on a first flow resistance within the first portion of the draw/return line, the first flow resistance calculated based on the at least one characteristic of the first portion of the draw/return line.

8. A method according to claim 5, wherein the flow rate is further controlled based on a second flow resistance within the second portion of the draw/return line, the second flow resistance calculated based on the at least one characteristic of the second portion of the draw/return line.

9. A method according to claim 1, wherein the blood component separation device further separates the drawn blood into a third blood component in addition to the first blood component and the second blood component.

10. A method according to claim 9, wherein the first blood component is red blood cells, the second blood component is platelets, and the third blood component is plasma.

11. A method according to claim 1, wherein the subject access pressure is determined in real-time.

12. A method according to claim 1, wherein the flow rate is at least one of a draw flow rate and a return flow rate.

* * * * *